US00PP26182P3

(12) United States Plant Patent
Kardos

(10) Patent No.: US PP26,182 P3
(45) Date of Patent: Dec. 1, 2015

(54) ***HYDRANGEA MACROPHYLLA* PLANT NAMED 'BOUNTIFUL BOUQUETS'**

(50) Latin Name: ***Hydrangea macrophylla* (Thunb.) Ser.**
Varietal Denomination: Bountiful Bouquets

(71) Applicant: Joshua H. Kardos, Watkinsville, GA (US)

(72) Inventor: Joshua H. Kardos, Watkinsville, GA (US)

(73) Assignees: Plant Introductions, Inc., Watkinsville, GA (US); University of Georgia Research Foundation, Inc., Athens, GA (US)

( * ) Notice: Subject to any disclaimer, the term of this patent is extended or adjusted under 35 U.S.C. 154(b) by 121 days.

(21) Appl. No.: 13/998,272

(22) Filed: Oct. 17, 2013

(65) Prior Publication Data

US 2014/0283252 P1 Sep. 18, 2014

Related U.S. Application Data

(60) Provisional application No. 61/784,698, filed on Mar. 14, 2013.

(51) Int. Cl.
*A01H 5/00* (2006.01)
*A01H 5/02* (2006.01)

(52) U.S. Cl.
USPC ..... Plt./250
CPC ..... *A01H 5/02* (2013.01)

(58) Field of Classification Search
USPC ..... Plt./250
See application file for complete search history.

*Primary Examiner* — Susan McCormick Ewoldt
(74) *Attorney, Agent, or Firm* — Lathrop & Gage LLP

(57) ABSTRACT

A new and distinct cultivar of *Hydrangea macrophylla* plant named 'Bountiful Bouquets', characterized by its remontant (reblooming) trait, flowering on old wood and new growth of the season; medium pink mophead inflorescences or medium blue inflorescences in non-aluminum or aluminum based media, respectively; compact, rounded growth habit; strong stems that hold the inflorescences upright; matte, dark green foliage; and moderate resistance to powdery mildew.

3 Drawing Sheets

Genus and species of plant claimed: *Hydrangea macrophylla* (Thunb.) Ser.
Variety denomination: 'Bountiful Bouquets'.

BACKGROUND OF THE INVENTION

The present invention relates to a new and distinct cultivar of *Hydrangea macrophylla*, a member of the Hydrangeaceae family, hereinafter referred to by its cultivar name 'Bountiful Bouquets'. This cultivar is grown primarily as an ornamental for landscape use and for use as a potted plant.

The cultivar originated from a controlled cross-pollination of *Hydrangea macrophylla* 'Mathilda Gutges' (unpatented) crossed with *Hydrangea macrophylla* 'David Ramsey' (unpatented) in Athens, Ga. in 2005, and was selected from the progeny of this cross by continued evaluation for growth habit, improved leaf and flower characteristics, and increased resistance to powdery mildew. The cultivar 'Bountiful Bouquets' originated and was discovered in a cultivated environment in Athens, Ga.

'Bountiful Bouquets' has been asexually reproduced by softwood cuttings since 2006 in Athens, Ga. and in Watkinsville, Ga. The characteristics of the cultivar have been stable and reproduced true to type in successive vegetative generations.

SUMMARY OF THE INVENTION

'Bountiful Bouquets' has not been observed under all possible environmental conditions. The phenotype may vary somewhat with changes in light, temperature, soil and rainfall without, however, any variance in genotype.

The following traits have been observed and represent the characteristics of the new cultivar. In combination these characteristics distinguish 'Bountiful Bouquets' from all other varieties in commerce known to the inventor. 1) Remontant (reblooming) trait, flowering on old wood and new growth of the season. 2) Medium pink mophead inflorescences or medium blue inflorescences in non-aluminum or aluminum based media, respectively. 3) Compact, rounded growth habit. 4) Strong stems that hold the inflorescences upright. 5) Matte, dark green foliage. 6) Moderate resistance to powdery mildew.

'Bountiful Bouquets' is distinguished from its female parent 'Mathilda Gutges' by its growth habit, and flower and foliage color, and by its reblooming trait. 'Bountiful Bouquets' has a larger, compact, rounded growth habit, medium pink or medium blue inflorescences, matte, dark green foliage, and is a rebloomer, whereas 'Mathilda Gutges' has an overall smaller, compact, rounded growth habit, rich pink or violet-blue inflorescences, lustrous, dark green foliage, and is not a rebloomer. 'Bountiful Bouquets' is distinguished from its male parent 'David Ramsey' by its flower and foliage color. 'Bountiful Bouquets' has medium pink or medium blue inflorescences and matte, dark green foliage, whereas 'David Ramsey' has lighter pink or lighter blue inflorescences and matte, medium green foliage. There are no other cultivars of *Hydrangea macrophylla* with this combination of traits known to the inventor.

'Bountiful Bouquets' can be compared to the cultivar 'Show Stopper' (U.S. Plant patent Ser. No. 13/998,265) but differs in the following characteristics. 'Bountiful Bouquets' has a larger, compact, rounded growth habit, whereas 'Show Stopper' has a smaller, compact, mounded growth habit. 'Bountiful Bouquets' has medium pink or medium blue inflorescences, whereas 'Show Stopper' has dark pink or dark blue inflorescences. 'Bountiful Bouquets' has matte, dark green foliage, whereas 'Show Stopper' has lustrous, dark green foliage.

BRIEF DESCRIPTION OF THE DRAWINGS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Hydrangea*.

DETAILED DESCRIPTION

Figure 1:
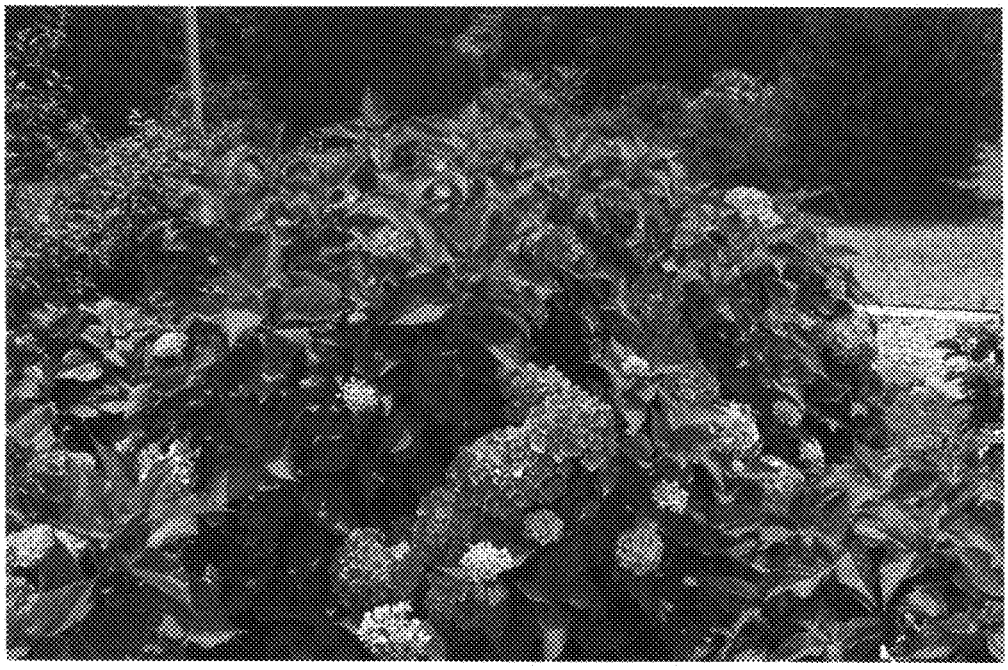
FIG. 1 illustrates a 'Bountiful Bouquets' plant grown in the ground in the presence of aluminum.
Figure 2:
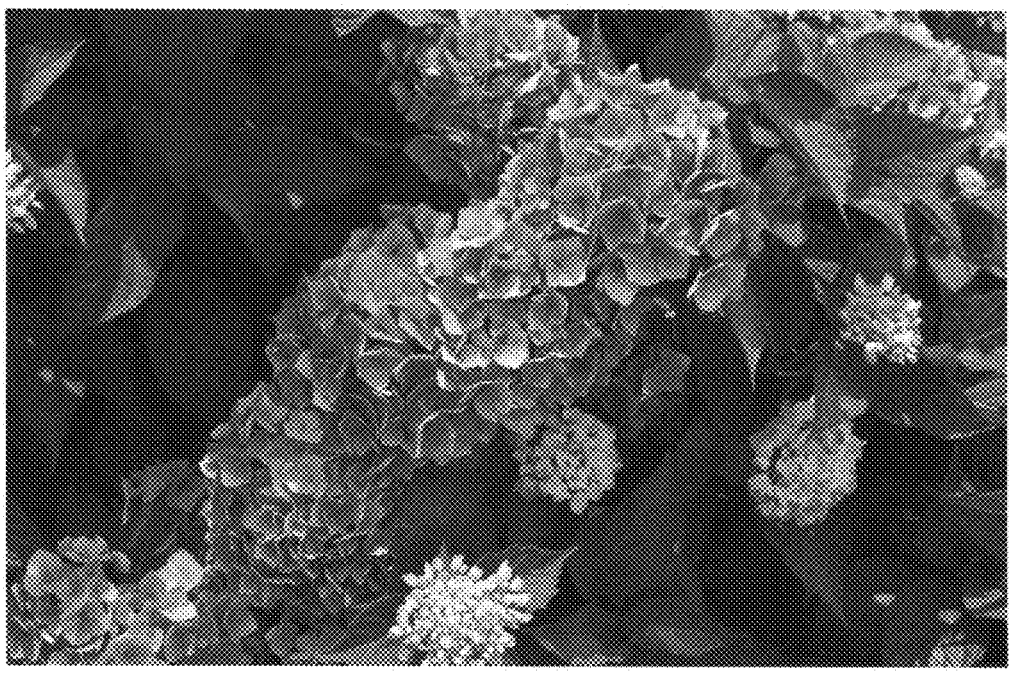
FIG. 2 illustrates an inflorescence on 'Bountiful Bouquets' grown in the presence of aluminum.
Figure 3:
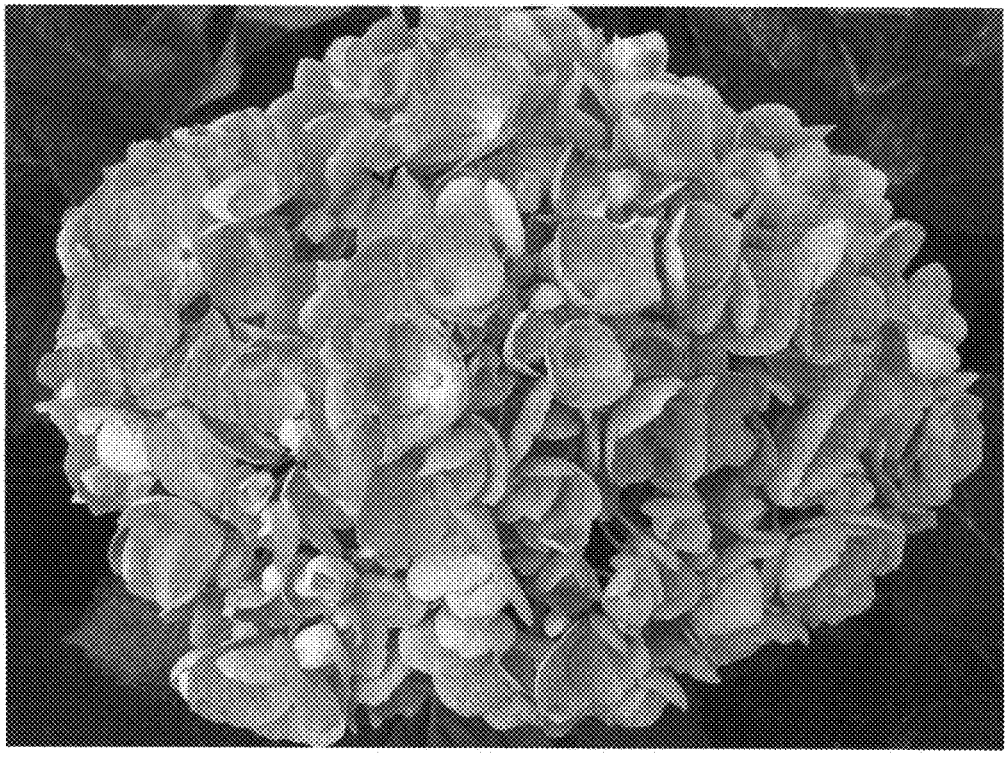
FIG. 3 illustrates an inflorescence on 'Bountiful Bouquets' grown in the absence of aluminum.

In the following description, color references are made to The Royal Horticultural Society Colour Chart, 2007 Edition, except where general terms of ordinary dictionary significance are used. Plants used for the description were grown in 11.8 L containers under 50% shade under outdoor conditions in a nursery in Watkinsville, Ga. Plants were about 2 years old when the description was recorded. Two groups of plants were used for the description to described the flower colors with and without aluminium. The first group was grown in a medium consisting of composted pine bark, with no aluminium present and a pH of 5.7. The second group was grown in a medium consisting of composted pine bark that was amended with 45 grams of aluminium sulphate and pH of 5.7. Aluminium only affects flower color. Therefore, colors with and without aluminium are only specified for floral parts.

Botanical classification: 'Bountiful Bouquets' is a cultivar of *Hydrangea macrophylla*.

Parentage: The current variety is a progeny from a controlled cross-pollination of *Hydrangea macrophylla* 'Mathilda Gutges' crossed with *Hydrangea* macrophylla 'David Ramsey'.

Propagation: Vegetatively by stem cuttings.

Plant description: The claimed variety is a compact, mounded deciduous shrub. The original plant, now about 8-years-old in the ground, is about 145 cm in height from the soil level to the top of the inflorescences, and about 216 cm in diameter. Freely branching. The plant is cold hardy in USDA Zones 5 to 9.

*Stems.*—First year stems have a diameter of about 7 mm, a round shape, and a stout, glabrous and lustrous texture with very fine pubescence.

*Exfoliation.*—On second year and older stems, flaky and stringy. Internodes have a length of about 7.3 cm. The stem color is 144A. Second year stems have a diameter of about 8 mm or more and are N199D in color.

*Vegetative buds.*—Arrangement: opposite.

*Shape.*—Ovoid.

*Size.*—About 4.5 mm in length, about 3 mm in width.

*Color.*—144B at the base, gradually changing to 183B at the apex.

Leaves:

*Size.*—About 16.6 cm in length and about 9 cm in width.

*Shape.*—Ovate, with acuminate apex, cuneate base and serrate margin.

*Texture.*—Thick and leathery.

*Color.*—Emerging leaves are 143A on the upper surface and 138B on the lower surface; mature leaves on the upper surface are N137A, and 138A on the lower surface.

*Venation.*—Pinnate, veins are 151C on the upper surface and 145C on the lower surfaces.

*Petiole.*—About 2.2 cm in length and about 4 mm in diameter, glabrous texture, and N144D in color.

Flowers:

*Inflorescence bloom period.*—Early summer to first frost in fall. An inflorescence contains about 88 individual fertile flowers. An inflorescence contains about 349 individual sterile florets.

*Inflorescence shape and size.*—Mophead, about 10.3 cm in height and about 17.8 cm in diameter. The inflorescence is effective for about 8 weeks. The peduncle is about 8.8 cm in length, is finely pubescent, and is 144A in color with aluminium and 128C in color without aluminum. The pedicels are about 2.2 cm in length, finely pubescent, and 76A in color with aluminum and 62C in color without aluminum.

*Flower bud size.*—About 3 mm in length, about 3.5 mm in diameter.

*Flower bud shape.*—Round. Color: 97A when grown with aluminum, and 85B when grown without aluminum.

*Sterile florets.*—Are about 3.7 cm in diameter. Each floret contains 4 sepals about 1.8 cm in length and about 1.8 cm in width.

*Sterile floret shape.*—Ovoid with obtuse apex, acute base, and entire margin.

*Texture.*—Smooth with no pubescence.

*Color at maturity.*—The upper surface is 94D and the lower surface is 92C with aluminum.

*Color at maturity.*—The upper surface is N80B and the lower surface is N78D without aluminum.

*Petals (fertile flowers).*—Size: 5 petals per flower, about 4 mm in length and about 2 mm in width.

*Shape.*—Ovate, with acuminate apex, truncate base, and entire margin.

*Texture.*—Smooth with no pubescence.

*Color.*—At peak of bloom the upper surface of the petals is 96D and the lower surface is 97A with aluminum.

*Color.*—At peak of bloom the upper surface of the petal is N82C and lower surface is N82D without aluminum.

*Number of stamens.*—6 to 10.

*Anthers.*—About 1 mm in length and about 0.5 mm in width, 97C in color with aluminum, and 84C in color without aluminum.

*Filaments.*—About 4 mm in length and 97D in color with aluminum, and 84D in color without aluminum.

*Pollen.*—NN155B in color, produced in moderate quantities.

*Pistil.*—Superior, about 3 mm in length and about 1.5 mm in width, 92C in color with aluminum, and N80B with no aluminum.

*Stigma.*—2 or 3 per pistil, round in shape and 97A in color with aluminum, and N82D with no aluminum.

*Style*.—About 2 mm in length and tubular in shape, 95C in color with aluminum, and N78D with no aluminum.

Fruit: The capsule fruit is ovoid, about 3 mm in length and about 2 mm in width. Color at maturity is 200C. The number of fruit per infructescence varies widely.

*Seed*.—The seeds are round, about 0.5 mm in length and about 0.5 mm in width, close to 199B, and each capsule contains about 50 seeds.

Disease/pest resistance: Moderately resistant to powdery mildew. No other pest or disease resistance/susceptibility has been observed. 'Bountiful Bouquets' is cold hardy from USDA Cold Hardiness Zones 5-9.

I claim:

1. A new and distinct *Hydrangea macrophylla* plant named 'Bountiful Bouquets', substantially as illustrated and described herein.

* * * * *